(12) United States Patent
Fan et al.

(10) Patent No.: US 11,813,418 B2
(45) Date of Patent: Nov. 14, 2023

(54) ECHOGENIC BALLOON DILATION CATHETER AND BALLOON THEREOF

(71) Applicant: BECTON, DICKINSON AND COMPANY, Franklin Lakes, NJ (US)

(72) Inventors: Qingqing Fan, Shanghai (CN); Irene Gao, Shanghai (CN); Xin Wen, Shanghai (CN)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 603 days.

(21) Appl. No.: 17/000,967

(22) Filed: Aug. 24, 2020

(65) Prior Publication Data

US 2021/0052861 A1 Feb. 25, 2021

(30) Foreign Application Priority Data

Aug. 22, 2019 (CN) .......................... 201921364734.2

(51) Int. Cl.
*A61M 25/10* (2013.01)

(52) U.S. Cl.
CPC . *A61M 25/1002* (2013.01); *A61M 2025/1075* (2013.01); *A61M 2025/1079* (2013.01); *A61M 2025/1086* (2013.01); *A61M 2025/1093* (2013.01); *A61M 2205/02* (2013.01)

(58) Field of Classification Search
CPC ...... A61M 25/1002; A61M 2025/1075; A61M 2025/1079; A61M 2025/1086; A61M 2025/1093; A61M 2205/02; A61M 25/10; A61M 25/0108
See application file for complete search history.

(56) References Cited

U.S. PATENT DOCUMENTS

| | | |
|---|---|---|
| 6,171,248 B1 | 1/2001 | Hossack et al. |
| 6,190,915 B1 | 2/2001 | Madsen et al. |
| 6,238,343 B1 | 5/2001 | Madsen et al. |
| 6,368,277 B1 | 4/2002 | Mao |
| 6,494,860 B2 | 8/2002 | Rocamora |
| 6,506,156 B1 * | 1/2003 | Jones ................... A61K 49/223 600/432 |
| 6,520,934 B1 | 2/2003 | Lee et al. |
| 6,540,721 B1 | 4/2003 | Voyles |
| 6,589,262 B1 | 7/2003 | Honebrink |
| 6,599,237 B1 | 7/2003 | Singh |
| 6,605,943 B1 | 8/2003 | Clark |
| 6,647,132 B1 | 11/2003 | Montillo |
| 6,663,595 B2 | 12/2003 | Spohn |

(Continued)

OTHER PUBLICATIONS

David Lewis, My patient is injured: Identifying foreign bodies with ultrasound, 2015, U.S. National Library of Medicine, Ultrasound vol. 23 (3), 174-180 (Year: 2015).*

*Primary Examiner* — Amber R Stiles
*Assistant Examiner* — Nelson Louis Alvarado, Jr.
(74) *Attorney, Agent, or Firm* — Dickinson Wright PLLC; Andrew D. Dorisio

(57) ABSTRACT

An echogenic balloon dilation catheter and a balloon thereof. The balloon includes a balloon body, a balloon cone at each side of the balloon body, and a balloon tip extending from the balloon cone and fixed to the catheter, the balloon body and the balloon cone being formed of a plurality of polymer layers in a radial direction of the balloon. The balloon may be of enhanced echogenicity using a variety of disclosed techniques.

12 Claims, 6 Drawing Sheets

(56) References Cited

U.S. PATENT DOCUMENTS

| | | |
|---|---|---|
| 6,673,060 B1 | 1/2004 | Fleming, III |
| 6,692,464 B2 | 2/2004 | Graf |
| 6,723,052 B2 | 4/2004 | Mills |
| 6,733,489 B2 | 4/2004 | Nutting |
| 6,736,803 B2 | 5/2004 | Cawood |
| 6,796,991 B2 | 5/2004 | Nardeo |
| 6,748,973 B2 | 6/2004 | Lindroos |
| 6,892,087 B2 | 5/2005 | Osypka |
| 6,905,458 B2 | 6/2005 | Choay et al. |
| 6,939,370 B2 | 9/2005 | Hartley |
| 7,001,369 B2 | 2/2006 | Griffin et al. |
| 7,001,396 B2 | 2/2006 | Glazier et al. |
| 7,048,717 B1 | 5/2006 | Frassica |
| 7,101,353 B2 | 9/2006 | Lui et al. |
| 7,104,979 B2 | 9/2006 | Jansen et al. |
| 7,153,277 B2 | 12/2006 | Skujins et al. |
| 7,158,692 B2 | 1/2007 | Chalana et al. |
| 7,217,256 B2 | 5/2007 | Di Palma |
| 7,258,669 B2 | 8/2007 | Russell |
| 7,276,062 B2 | 10/2007 | McDaniel et al. |
| 7,306,585 B2 | 12/2007 | Ross |
| 7,314,481 B2 | 1/2008 | Karpiel |
| 7,322,959 B2 | 1/2008 | Warnack et al. |
| 7,462,488 B2 | 12/2008 | Madsen et al. |
| 7,481,805 B2 | 1/2009 | Magnusson |
| 7,510,568 B2 | 3/2009 | Bleam et al. |
| 7,524,305 B2 | 4/2009 | Moyer |
| 7,534,250 B2 | 5/2009 | Schaeffer et al. |
| 7,578,814 B2 | 8/2009 | Accisano, III et al. |
| 7,591,813 B2 | 9/2009 | Levine et al. |
| 7,655,021 B2 | 2/2010 | Brasington et al. |
| 7,677,078 B2 | 3/2010 | Sauer et al. |
| 7,678,100 B2 | 3/2010 | Chin et al. |
| 7,704,245 B2 | 4/2010 | Dittman et al. |
| 7,722,567 B2 | 5/2010 | Tal |
| 7,736,331 B2 | 6/2010 | Accisano, III et al. |
| 7,780,715 B2 | 8/2010 | Shaked et al. |
| 7,794,402 B2 | 9/2010 | Wang |
| 7,833,597 B2 | 11/2010 | Bavaro et al. |
| 7,857,820 B2 | 12/2010 | Skakoon et al. |
| 7,874,987 B2 | 1/2011 | Altmann et al. |
| 7,875,021 B2 | 1/2011 | Minassians |
| 7,879,024 B2 | 2/2011 | Thorstenson et al. |
| 7,909,798 B2 | 3/2011 | Osypka |
| 7,909,814 B2 | 3/2011 | Accisano, III et al. |
| 7,922,696 B2 | 4/2011 | Tal et al. |
| 7,951,093 B2 | 5/2011 | Skujins et al. |
| 7,961,929 B2 | 6/2011 | Ni et al. |
| 7,968,038 B2 | 6/2011 | Dittman et al. |
| 7,985,232 B2 | 7/2011 | Potter et al. |
| 7,993,272 B2 | 8/2011 | Chomas et al. |
| 7,993,305 B2 | 8/2011 | Ye et al. |
| 8,070,694 B2 | 12/2011 | Galdonik et al. |
| 8,105,287 B2 | 1/2012 | Fisher et al. |
| 8,137,309 B2 | 3/2012 | Nishtala et al. |
| 8,137,317 B2 | 3/2012 | Osypka |
| 8,147,452 B2 | 4/2012 | Nardeo et al. |
| 8,147,456 B2 | 4/2012 | Fisher et al. |
| 8,157,790 B2 | 4/2012 | Kubo et al. |
| 8,177,770 B2 | 5/2012 | Rasmussen et al. |
| 8,262,671 B2 | 9/2012 | Osypka |
| 8,273,059 B2 | 9/2012 | Nardeo et al. |
| 8,287,585 B2 | 10/2012 | Gurm |
| 8,292,852 B2 | 10/2012 | Mulholland et al. |
| 8,366,674 B2 | 2/2013 | Frassica et al. |
| 8,377,083 B2 | 2/2013 | Mauch et al. |
| 8,460,323 B2 | 6/2013 | Mauch et al. |
| 8,478,383 B2 | 7/2013 | Bar-Tal et al. |
| 8,500,688 B2 | 8/2013 | Engel et al. |
| 8,517,993 B2 | 8/2013 | Freas et al. |
| 8,591,567 B2 | 11/2013 | Chau et al. |
| 8,639,310 B2 | 1/2014 | Chen et al. |
| 8,652,098 B2 | 2/2014 | Haslinger |
| 8,696,582 B2 | 4/2014 | Rohling |
| 8,700,129 B2 | 4/2014 | Hauck et al. |
| 8,734,426 B2 | 5/2014 | Ahmed et al. |
| 8,753,313 B2 | 6/2014 | Kimmel et al. |
| 8,771,225 B2 | 7/2014 | Ahn |
| 8,795,311 B2 | 8/2014 | Griffith et al. |
| 8,827,958 B2 | 9/2014 | Bierman et al. |
| 8,834,499 B2 | 9/2014 | Mauch et al. |
| 8,845,614 B2 | 9/2014 | Raabe et al. |
| 8,888,787 B2 | 11/2014 | Wynberg |
| 8,906,268 B2 | 12/2014 | Boutet et al. |
| 8,911,400 B2 | 12/2014 | Ferry |
| 8,926,560 B2 | 1/2015 | Dinh et al. |
| 8,948,474 B2 | 2/2015 | Chang et al. |
| 8,986,283 B2 | 3/2015 | Rajendran et al. |
| 8,998,814 B2 | 4/2015 | Oikawa et al. |
| 9,044,266 B2 | 6/2015 | Nimgaard |
| 9,044,577 B2 | 6/2015 | Bishop et al. |
| 9,060,756 B2 | 6/2015 | Bencini et al. |
| 9,089,672 B2 | 7/2015 | Hendriksen et al. |
| 9,126,019 B2 | 9/2015 | Guo et al. |
| 9,149,176 B2 | 10/2015 | Greenberg et al. |
| 9,149,606 B2 | 10/2015 | Beissel et al. |
| 9,174,036 B2 | 11/2015 | Okamura et al. |
| 9,186,484 B2 | 11/2015 | Defossez et al. |
| 9,233,226 B2 | 1/2016 | Lampropoulos et al. |
| 9,241,735 B2 | 1/2016 | Nishtala et al. |
| 9,242,076 B2 | 1/2016 | Burton et al. |
| 9,248,261 B2 | 2/2016 | Schweikert et al. |
| 9,254,146 B2 | 2/2016 | Massengale et al. |
| 9,282,945 B2 | 3/2016 | Smith et al. |
| 9,314,749 B2 | 4/2016 | Yagi et al. |
| 9,352,132 B2 | 5/2016 | Urie |
| 9,393,041 B2 | 7/2016 | Barker et al. |
| 9,398,936 B2 | 7/2016 | Razzaque et al. |
| 9,409,001 B2 | 8/2016 | Aggerholm et al. |
| 9,420,992 B2 | 8/2016 | Sheldon et al. |
| 9,445,837 B2 | 9/2016 | Fulton, III |
| 9,474,882 B2 | 10/2016 | Franklin |
| 9,492,638 B2 | 11/2016 | McKinnis et al. |
| 9,498,282 B2 | 11/2016 | Fernald |
| 9,504,476 B2 | 11/2016 | Gulachenski |
| 9,517,185 B1 | 12/2016 | Al-Jazaeri |
| 9,522,253 B2 | 12/2016 | Gandras et al. |
| 9,538,981 B2 | 1/2017 | Rioux et al. |
| 9,539,415 B2 | 1/2017 | Racz et al. |
| 9,545,506 B2 | 1/2017 | Quigley |
| 9,566,087 B2 | 2/2017 | Bierman et al. |
| 9,566,413 B2 | 2/2017 | Eberhardt et al. |
| 9,629,981 B2 | 4/2017 | Thungana et al. |
| 9,655,594 B2 | 5/2017 | Oraevsky et al. |
| 9,668,654 B2 | 6/2017 | Rajendran et al. |
| 9,693,820 B2 | 7/2017 | Potter et al. |
| 9,706,988 B2 | 7/2017 | Nobles et al. |
| 9,717,884 B2 | 8/2017 | Matsumoto et al. |
| 9,737,284 B2 | 8/2017 | Kim et al. |
| 9,764,111 B2 | 9/2017 | Gulachenski |
| 9,764,117 B2 | 9/2017 | Bierman et al. |
| 9,773,307 B2 | 9/2017 | Chang et al. |
| 9,839,770 B2 | 12/2017 | Linden et al. |
| 9,861,385 B2 | 1/2018 | Fulton |
| 9,872,666 B2 | 1/2018 | Quearry |
| 9,877,704 B2 | 1/2018 | Ogawa |
| 9,884,169 B2 | 2/2018 | Bierman et al. |
| 9,920,188 B2 | 3/2018 | Vogt et al. |
| 9,950,158 B2 | 4/2018 | True et al. |
| 9,955,940 B1 | 5/2018 | Coats et al. |
| 9,972,082 B2 | 5/2018 | Holsing et al. |
| 9,980,699 B2 | 5/2018 | Quearry et al. |
| 10,004,475 B2 | 6/2018 | Quearry |
| 10,010,701 B2 | 7/2018 | Ahmed et al. |
| 10,034,655 B2 | 7/2018 | McKinnis et al. |
| 10,074,037 B2 | 9/2018 | Lu et al. |
| 10,076,307 B2 | 9/2018 | Coats et al. |
| 10,080,873 B2 | 9/2018 | Stapleton et al. |
| 10,086,174 B2 | 10/2018 | Crall et al. |
| 10,111,645 B2 | 10/2018 | Fearnot et al. |
| 10,118,027 B2 | 11/2018 | Seifert et al. |
| 10,137,020 B2 | 11/2018 | Treacy et al. |
| 10,143,455 B2 | 12/2018 | Lichty, II et al. |
| 10,166,070 B2 | 1/2019 | Davies et al. |

(56) References Cited

U.S. PATENT DOCUMENTS

| | | |
|---|---|---|
| 10,169,641 B2 | 1/2019 | Lee et al. |
| 10,173,033 B2 | 1/2019 | Leung et al. |
| 10,182,804 B2 | 1/2019 | Walters et al. |
| 10,183,147 B2 | 1/2019 | Yang et al. |
| 10,188,371 B2 | 1/2019 | Madsen et al. |
| 10,213,582 B2 | 2/2019 | Garrison et al. |
| 10,213,583 B2 | 2/2019 | Klocke et al. |
| 10,219,788 B2 | 3/2019 | Tabeie |
| 10,220,192 B2 | 3/2019 | Drasler et al. |
| 10,226,203 B2 | 3/2019 | Stigall et al. |
| 10,226,264 B2 | 3/2019 | McIntosh et al. |
| 10,238,463 B2 | 3/2019 | Verstege et al. |
| 10,238,834 B2 | 3/2019 | Bridgeman et al. |
| 10,249,037 B2 | 4/2019 | Chang et al. |
| 10,252,028 B2 | 4/2019 | Katsurada et al. |
| 2006/0182873 A1 * | 8/2006 | Klisch ............... A61M 25/10 427/2.1 |
| 2008/0132933 A1 | 6/2008 | Gerber |
| 2009/0030370 A1 | 1/2009 | Nishtala et al. |
| 2010/0234875 A1 * | 9/2010 | Allex ............... A61M 25/104 606/191 |
| 2011/0181614 A1 | 7/2011 | Chang et al. |
| 2011/0224538 A1 | 9/2011 | Linares |
| 2012/0209176 A1 * | 8/2012 | Anderson ......... A61M 25/1006 604/103.02 |
| 2012/0232528 A1 * | 9/2012 | Eli .................... A61M 25/0108 604/529 |
| 2013/0103004 A1 | 4/2013 | Gray et al. |
| 2013/0190609 A1 | 7/2013 | Fischer, Jr. |
| 2013/0226094 A1 | 8/2013 | Ahmed et al. |
| 2014/0180068 A1 | 6/2014 | Spencer et al. |
| 2014/0206987 A1 | 7/2014 | Urbanski et al. |
| 2014/0221828 A1 | 8/2014 | McKinnis et al. |
| 2014/0257090 A1 | 9/2014 | Fischer, Jr. et al. |
| 2014/0265024 A1 | 9/2014 | Quearry |
| 2014/0276073 A1 | 9/2014 | Quearry |
| 2015/0086094 A1 | 3/2015 | Chang et al. |
| 2015/0086095 A1 | 3/2015 | Chang et al. |
| 2015/0112256 A1 | 4/2015 | Byrne et al. |
| 2015/0150586 A1 | 6/2015 | Aggerholm et al. |
| 2015/0272542 A1 | 10/2015 | Shuman et al. |
| 2015/0273120 A1 | 10/2015 | Zamarripa et al. |
| 2015/0320979 A1 | 11/2015 | Fearnot et al. |
| 2016/0120509 A1 | 5/2016 | Syed et al. |
| 2016/0128718 A1 | 5/2016 | Aggerholm et al. |
| 2016/0193448 A1 | 7/2016 | Nardeo et al. |
| 2016/0223308 A1 | 8/2016 | Rhee et al. |
| 2016/0331929 A1 | 11/2016 | Lampropoulos et al. |
| 2017/0021139 A1 | 1/2017 | Bajema et al. |
| 2017/0032557 A1 | 2/2017 | Anand et al. |
| 2017/0049997 A1 | 2/2017 | Chao et al. |
| 2017/0112528 A1 | 4/2017 | Crisman et al. |
| 2017/0135908 A1 | 5/2017 | Tai et al. |
| 2017/0143349 A1 | 5/2017 | Raabe et al. |
| 2017/0151415 A1 | 6/2017 | Maeda et al. |
| 2017/0173302 A1 | 6/2017 | Beasley et al. |
| 2017/0182297 A1 | 6/2017 | Lysgaard et al. |
| 2017/0182304 A1 | 6/2017 | Bagwell et al. |
| 2017/0189059 A1 | 7/2017 | Long, Jr. et al. |
| 2017/0224967 A1 | 8/2017 | Gorn et al. |
| 2017/0232231 A1 | 8/2017 | Neoh et al. |
| 2017/0252560 A1 | 9/2017 | Imran |
| 2017/0296798 A1 | 10/2017 | Kume et al. |
| 2017/0333149 A1 | 11/2017 | Stigall et al. |
| 2017/0333682 A1 | 11/2017 | Nardeo |
| 2017/0368238 A1 | 12/2017 | Robinson |
| 2018/0001063 A1 | 1/2018 | Aggerholm et al. |
| 2018/0008237 A1 | 1/2018 | Venkataraman et al. |
| 2018/0015277 A1 | 1/2018 | Stephens et al. |
| 2018/0036033 A1 | 2/2018 | Ignagni et al. |
| 2018/0093073 A1 | 4/2018 | Shimizu et al. |
| 2018/0117279 A1 | 5/2018 | Yachia et al. |
| 2018/0126129 A1 | 5/2018 | McDonough |
| 2018/0132821 A1 | 5/2018 | Dehghan Marvast et al. |
| 2018/0169383 A1 | 6/2018 | Khalaj et al. |
| 2018/0177980 A1 | 6/2018 | Khalaj et al. |
| 2018/0200491 A1 * | 7/2018 | Giasolli ............ A61M 25/1029 |
| 2018/0214288 A1 | 8/2018 | Smouse et al. |
| 2018/0221649 A1 | 8/2018 | Mulrooney et al. |
| 2018/0243046 A1 | 8/2018 | Scott et al. |
| 2018/0256849 A1 | 9/2018 | Linden et al. |
| 2018/0256907 A1 | 9/2018 | Katra et al. |
| 2018/0263595 A1 | 9/2018 | Goksel et al. |
| 2018/0272039 A1 | 9/2018 | Kim et al. |
| 2018/0296186 A1 | 10/2018 | Harks et al. |
| 2018/0296804 A1 | 10/2018 | Bierman |
| 2018/0360494 A1 | 12/2018 | Melsheimer |
| 2019/0001031 A1 | 1/2019 | Real et al. |
| 2019/0015638 A1 | 1/2019 | Gruba et al. |
| 2019/0053790 A1 | 2/2019 | Grover et al. |
| 2019/0059857 A1 | 2/2019 | Ogura et al. |
| 2019/0076166 A1 | 3/2019 | Bierman et al. |
| 2019/0076167 A1 | 3/2019 | Fantuzzi et al. |
| 2019/0083061 A1 | 3/2019 | Choi |
| 2019/0091453 A1 | 3/2019 | Browne et al. |
| 2019/0091461 A1 | 3/2019 | Bonham et al. |
| 2019/0105466 A1 | 4/2019 | Schibli et al. |
| 2019/0105474 A1 | 4/2019 | Sheibley |
| 2019/0110795 A1 | 4/2019 | Koo et al. |
| 2019/0125318 A1 | 5/2019 | Sarna et al. |
| 2019/0125398 A1 | 5/2019 | Baldwin et al. |

* cited by examiner

ECHOGENIC BALLOON DILATION CATHETER AND BALLOON THEREOF

This application claims the benefit of Chinese Patent Application No. 201910775996.6 and Chinese Utility Model No. 201921364734.2, both filed Aug. 22, 2019, the disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure relates to a balloon dilation catheter and a balloon thereof, as an effective dilation device for percutaneous nephrolithotomy (PCNL) surgery, for example. In particular, the present disclosure relates to a balloon dilation catheter and a balloon thereof for easy identification.

BACKGROUND

Balloon dilatation catheters are currently widely used in many fields, including blood vessel dilation, stent placement, and creation of kidney calculi removal channels.

Desirable properties of balloon dilatation catheters are high burst pressure and distal positionability.

Distal Positionability

For doctors, it is desirable to determine a distal position of a balloon and an effective portion of the balloon in accidentally injured patients so as to better treat the patients.

For example, for percutaneous nephrolithotomy (PCNL), if blind puncture is performed during the dilation procedure, this will bring a high risk of puncture failure or damage to the renal parenchyma. Therefore, surgeons urgently need percutaneous devices (especially the distal end portion) that can be seen by medical imaging methods so as to reduce the risk during puncture. In the United States, a measure for visible PCNL is to perform surgery under X-ray such that a part of the device with X-ray opacity can be seen in images. However, it is commonly known that X-ray radiation is harmful to health of patients and doctors. Further, an X-ray image actually shows a two-dimensional structure instead of a three-dimensional structure, which makes it difficult to determine a penetration depth of the device.

In most balloon dilatation catheters on the market, the distal end is examined by fluoroscopy rather than ultrasound. In China, most doctors are willing to perform surgery under ultrasound guidance. However, since it is difficult to locate the medical device with ultrasound during surgery, accidental injuries may be caused to patients. Some doctors inject an ultrasound contrast agent into a body of a balloon for examination during an operation. However, the distal end of the balloon still cannot be visually seen.

Therefore, with the increasing need for PCNL under the help of ultrasonic examination, doctors and medical device manufacturers have noticed a safe medical image measure that does not cause radiation damage to patients and doctors. A device with echogenicity is displayed as a bright area, which is easy to be seen in a grayscale ultrasound image.

The echogenic medical device appears as a bright shadow in the grayscale image captured by a B-type ultrasonic instrument, enabling an operator to distinguish the difference in brightness between the medical device and a surrounding tissue in the image. A key factor in obtaining a bright shadow is that a probe can receive more backscatter from a surface of the device. In order to design a surface with higher backscatter, an interface with a high acoustic impedance difference (Z) should be created between the tissue and the surface of the medical device so that high frequency acoustic pulses can be reflected. Theoretically, the higher acoustic impedance difference at the interface should be set such that: the more the 180° reflection is, the better the echogenicity is detected. As shown in equation $Z=\rho \times v$, Z is the product of density of material and propagation speed of sound wave in the material. Since the surrounding tissue and environment of the balloon dilator in the kidney during the PCNL is the renal cortex and renal pelvis filled with saline, the surface of the echogenic balloon dilator should have a significant density difference and a sound wave passing speed difference as compared to the renal cortex and renal pelvis.

An effective way is to create a gas-solid interface or a liquid-solid interface, because there are density difference and sound velocity difference between them. Among various materials, the Z value of air is extremely low, and the Z value of metal is higher than that of any polymer and liquid. Therefore, there are several ways to increase the difference in Z value at the interface, such as integrating metal materials, patterning the surface, or trapping gas at the device surface.

US2014/0243845A1 discloses a double-walled balloon catheter including an echogenic layer or sleeve made of 50%-85% metallic material mixed with polymer. US2013/0053770A1 also discloses a balloon catheter having at least two layers, one of which is made of a mixture of 80% tungsten and 20% polymer.

US2012/0277586A1 discloses an echogenic feeding tube having a metal sleeve, internal cannulas, or coiled ribbons or wrapped wires on the tubular member inside the balloon. US20080058702A1 discloses a catheter shaft which is wound with a coiled ribbon or a ribbon with a deformed surface. The metal part can also be processed by sand blasting, physical deformation or machining so as to have surface roughness and improve echogenicity.

US2008/0097213A1, US20150165160A1, U.S. Pat. Nos. 5,967,988 and 5,490,521A disclose various patterned surfaces for echogenic catheters and biopsy forceps. These patterns include spherical or hemispherical holes on a drainage catheter, laser-processed depressions with different angles on a surface of a cannula, convex, concave or other shapes of metal members embedded in a catheter body for coronary sinus perfusion.

Some examples of using gas, bubble, or fluid to improve echogenicity are listed as below. WO2007/102909A2 discloses an echogenicity blocking balloon by adding a polymer fluid cavity in a balloon body. U.S. Pat. No. 6,106,473 and WO98/19713 disclose porous polymer coatings with a large number of gas/non-gas interfaces, which are constructed by physical agitation and chemical reactions between mixed components that can release gas or H2O or are constructed only by volatilization of a volatile solvent. U.S. Pat. No. 6,506,156B1 discloses an echogenic coating with multiple pores or glass microsphere particles.

High Burst Pressure

Some materials are visible under ultrasound. However, it is difficult to combine these materials well with a balloon tip (also called as a neck) under a high pressure. If these materials are used to directly manufacture the balloon tip, a burst pressure of the balloon dilatation catheter will be greatly reduced.

At present, ultrasonic equipment and ultrasonic technology for detecting a target as accurately as an X-ray has not been fully developed, especially for complex detection environments. Since kidney calculi generally have high ultrasound echo signals (eg percutaneous nephrolithotomy), it is difficult to distinguish the balloon tip from the calculi under ultrasound, even if in the case where the balloon tip is made of a material with a high ultrasound echo signal.

Other Issues

During surgery, especially interventional surgery, it is difficult to measure the size of an affected area, such as the size of an aneurysm neck or the size of kidney calculi. Sometimes, it is important for doctors to get to know this information.

Further, for certain procedures (such as PCNL), only a portion of the balloon body is inserted into the patient. It is inconvenient for the surgeon to observe an insertion depth with naked eyes, so that the medical device cannot be placed correctly and may cause accidental injury.

SUMMARY

The present disclosure aims to solve at least one of the above problems, and possibly others that have yet to be discovered.

According to one aspect of the present disclosure, a special balloon tip design (including the design of the shape) helps to identify the balloon tip.

According to another aspect of the present disclosure, a special balloon body design also helps to identify the balloon body.

According to yet another aspect of the present disclosure, adding scale marks on the balloon will help the surgeon visually observe an insertion depth such that a medical device can be correctly placed without causing accidental injury. By placing a balloon with scale marks close to an affected area, it is helpful to determine a size of the affected area.

According to an aspect of the present disclosure, there is provided a balloon for a balloon dilatation catheter, comprising, along an axial direction of the balloon, a balloon body, a balloon cone at each side of the balloon body, and a balloon tip extending from the balloon cone and fixed to the catheter, the balloon body and the balloon cone being formed of a plurality of polymer layers in a radial direction of the balloon, characterized in that the balloon tip comprises metal.

According to an embodiment, the balloon tip is made entirely of metal.

According to an embodiment, a plurality of notches are formed on the metal balloon tip.

According to an embodiment, the balloon tip, balloon body, and balloon cones are all formed of multiple polymer layers in the radial direction of the balloon, and the balloon tip is covered with a metal sleeve or cladding layer.

According to an embodiment, the metal sleeve or cladding layer is subjected to rough surface treatment.

According to an embodiment, the surface treatment is sand blasting, physical deformation or machining.

According to an embodiment, the balloon tip, balloon body, and balloon cones are all formed of multiple polymer layers in the radial direction of the balloon, and the balloon tip is provided with a plurality of metal cuffs spaced apart in the axial direction and extending in a circumferential direction.

According to an embodiment, a surface of the metal balloon tip is patterned to form a rectangular array, a triangular array, a hemispherical array, a diamond array, a cylindrical array, or a plurality of parallel grooves extending in the circumferential direction.

According to an embodiment, the patterned surface of the metal balloon tip is covered with a heat-shrinkable polymer coating.

According to an embodiment, the balloon tip, balloon body, and balloon cones are all formed of multiple polymer layers in the radial direction of the balloon, and the balloon tip is wound with a metal fiber.

According to an embodiment, a metal echogenic layer is provided under an outermost polymer layer of the balloon.

According to an embodiment, the metal echogenic layer includes a plurality of metal cuffs spaced apart in the axial direction and extending in the circumferential direction of the balloon.

According to an embodiment, the plurality of polymer layers include a polymer adhesive layer, and metal powder is mixed in the polymer adhesive layer.

According to an embodiment, the plurality of polymer layers include a polymer adhesive layer, and bubbles or pores are formed in the polymer adhesive layer.

According to an embodiment, the balloon tip, balloon body and balloon cones are all formed of multiple polymer layers in the radial direction of the balloon, an integral metal ring is provided on the balloon tip, a body of the ring is provided thereon with a plurality of circumferentially extending through grooves with opening directions opposite to each other and spaced apart from each other in the axial direction.

According to an embodiment, the balloon tip, balloon body and balloon cones are all formed of multiple polymer layers in the radial direction of the balloon, an integral metal ring is provided on the balloon tip, and a body of the ring is provided thereon with a continuously spiral through groove.

According to an embodiment, the balloon tip, balloon body and balloon cone are all formed of multiple polymer layers in the radial direction of the balloon, an integral metal ring is provided on the balloon tip, and a body of the ring is provided thereon with a plurality of axially disposed windows with every two adjacent rows of windows staggered from each other in the circumferential direction.

According to an embodiment, scale marks capable of reflecting ultrasonic waves are printed on an outer surface of the balloon body.

According to an embodiment, a first scale mark and scale marks at regular intervals therefrom are different in shape from other scale marks.

According to an embodiment, a starting position of the scale marks may start at a distal end of the balloon or at a distance from the balloon tip.

According to another aspect of the present application, there is provided a balloon dilatation catheter including the balloon as described above and a catheter passing through an interior of the balloon.

BRIEF DESCRIPTION OF THE DRAWINGS

Other features of the present disclosure will become apparent from the following description of exemplary embodiments with reference to the drawings.

FIGS. 6A, 6B, and 6C each show an echogenic balloon tip with a differently patterned surface of;

DETAILED DESCRIPTION

Hereinafter, embodiments of the present disclosure will be described with reference to the accompanying drawings. An echogenic balloon dilatation catheter is an example of an echogenic medical device, such as for PCNL. However, it should be noted that examples of an echogenic medical device are not limited thereto.

Depending on specific applications, the echogenic medical devices may be other medical devices known to those skilled in the art, such as abdominal medical devices, gynecological and obstetric medical devices, cardiac medical devices, and so on.

Embodiments described below serve only as specific examples. However, the present disclosure is not limited to the embodiments described in the description.

Figure 1:
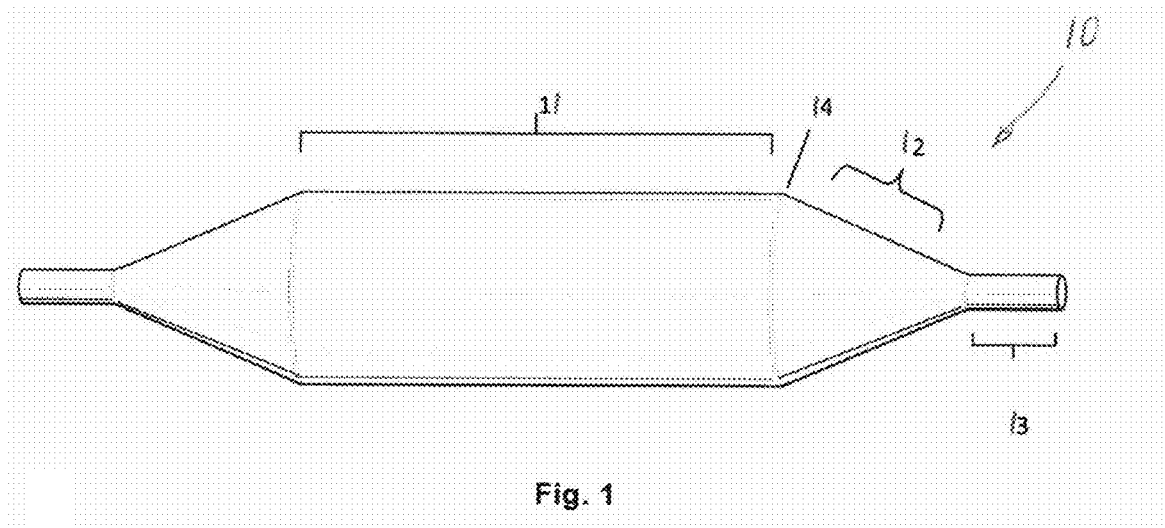
FIG. 1 shows a metal tip of an echogenic balloon.

In general, as shown in FIG. 1, a balloon for a balloon dilatation catheter is shown. The balloon 10 includes a cylindrical balloon body 11, a balloon cone 12 on each side of the balloon body, and a balloon tip (or balloon neck) 13 extending from the cone and fixed to the catheter. The balloon body merges with the balloon cone through a balloon shoulder 14.

An Echogenic Balloon Having an Echogenic Tip

More specifically, the present disclosure relates to an echogenic tip of a balloon. A balloon with an echogenic tip can be identified from a surrounding tissue and saline injected into a renal pelvis. The present disclosure can enhance the difference in acoustic impedance between the tip of the balloon and the surrounding environment.

Embodiment 1: An Echogenic Balloon Having a Metal Tip

As shown in FIG. 1, a distal tip 13 of the balloon connected to the cone of the balloon may be made of a metal material. Metal has a higher acoustic impedance value (Z value) than an organ tissue and an organ fluid, which helps to construct an interface with a significant Z value difference. Suitable metals include but are not limited to titanium, platinum, and stainless steel. They have excellent biocompatibility and can be used to process metal tubes. The metal tip is connected to the balloon cone by welding or bonding. The metal surface enhances the reflection of sound waves back to the ultrasonic probe.

Figure 2:
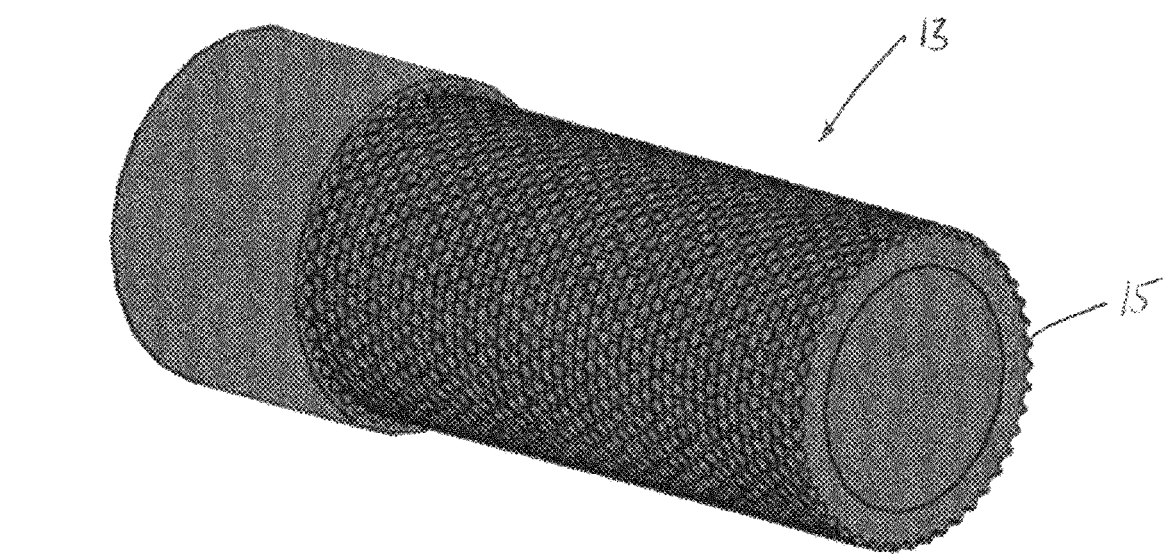
FIG. 2 shows an echogenic balloon tip with a notch.

A further modification is shown in FIG. 2, in which the tip 13 of the balloon is provided with notches 15 to enhance echogenicity, since backscattering of sound waves is enhanced. The notches 15 may be hemispherical, but could take other shapes as well. Each notch 15 may have a diameter of from about 20 μm to about 50 μm. The notches 15 may be formed using laser ablation on a smooth metal tip.

Figure 3:
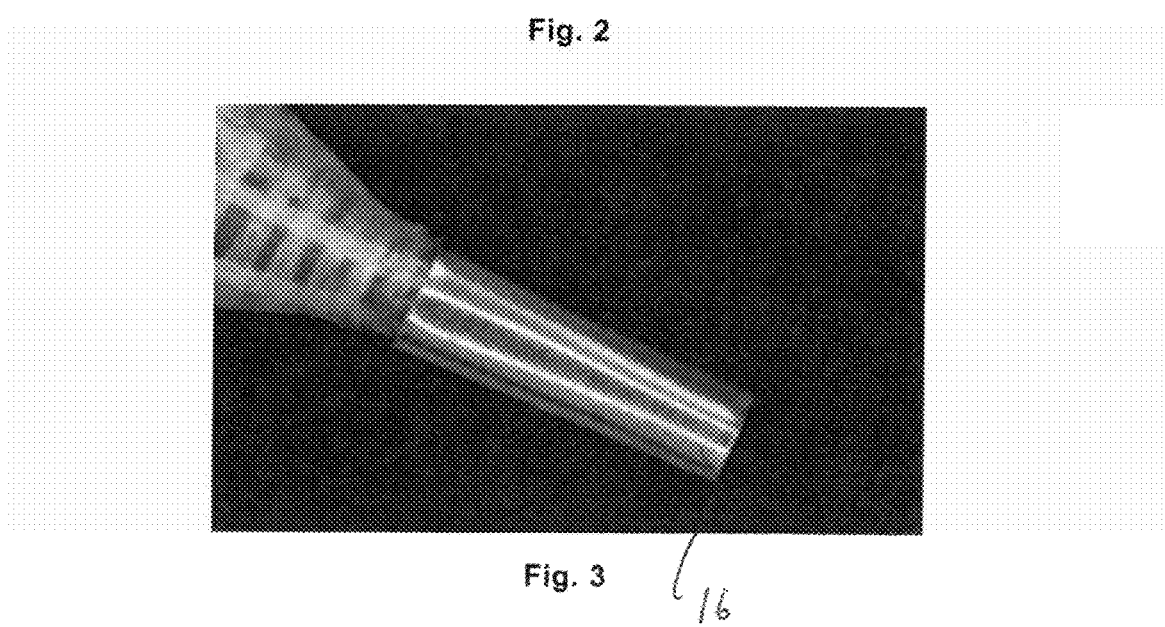
FIG. 3 shows an echogenic balloon tip with a metal sleeve or a cladding layer.

Embodiment 2: An Echogenic Balloon Tip with a Metal Sleeve or Cladding Layer As shown in FIG. 3, a sleeve or cladding layer 16 on the balloon tip 13 can improve the echogenicity of the balloon tip, since the difference in acoustic impedance at the interface increases. The advantage of the metal sleeve is that it is easy to adhere with an adhesive. Titanium, platinum or gold foil with a thickness of from about 0.01 mm to about 0.05 mm can be selected, since these metals with such a thickness are flexible enough for being wrapped on the balloon tip. All metals with good flexibility can be used. A titanium, platinum or gold tube with a wall thickness of from about 0.02 mm to about 0.05 mm is preferable, because a tube with such a wall thickness is sufficiently rigid to form a sleeve.

Figure 4:
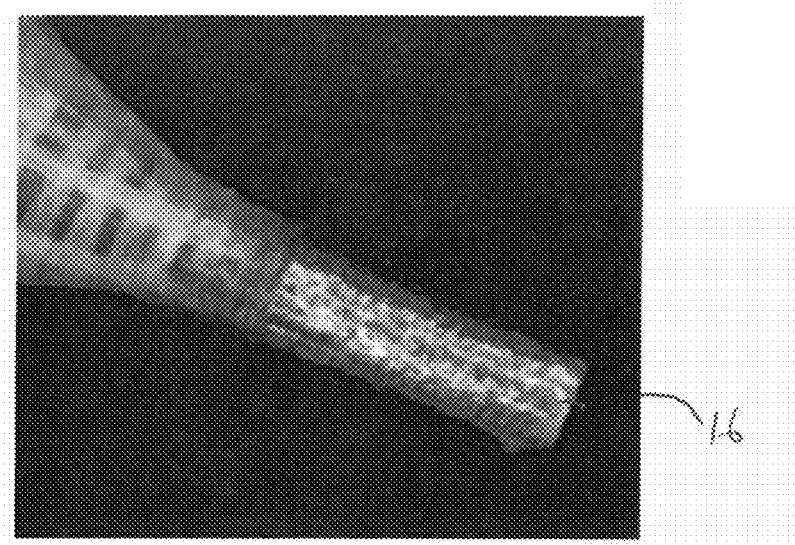
FIG. 4 shows an echogenic balloon tip subjected to surface treatment.

FIG. 4 shows a further improvement. Sandblasting (60-120 mesh) or physical deformation or machining is used to process the surface of the metal sleeve 16 or cladding layer so that the surface has a roughness of a few microns to tens of microns. This roughened surface can further improve the echogenicity, since back scattering of the sound is improved.

Embodiment 3: An Echogenic Balloon Tip with a Plurality of Metal Cuffs

Figure 5:
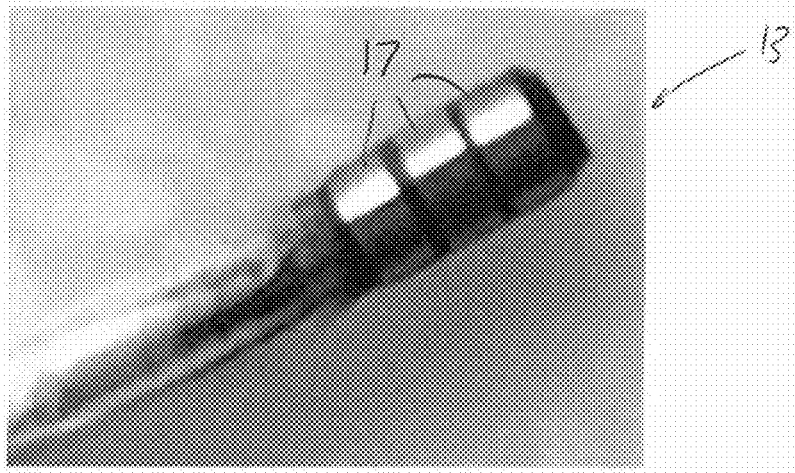
FIG. 5 shows an echogenic balloon tip with a plurality of metal cuffs.

As shown in FIG. 5, a plurality of metal cuffs 17 adhered to the balloon tip in the winding direction (that is, the circumferential direction) and spaced apart in the axial direction can improve the echogenicity of the tip, since the interface between the metal and the surrounding environment has a large difference in acoustic impedance. The metal may be titanium, platinum, gold, stainless steel or other metals with excellent biocompatibility. It is easy to adhere the cuffs on the surface of the balloon tip. It is only required that the adhesive is used to adhere the metal cuffs to the tip of the balloon, no matter whether an adhesive is applied densely or intermittently. Such a balloon tip can improve identifiability, because the adhered cuffs can appear as bright and dark intervals in the ultrasound image. The cuff has a thickness in range of from about 0.01 mm to about 0.05 mm, a width in range of from about 0.7 mm to about 2 mm, and an interval between adjacent cuffs of from about 0.5 mm to about 2 mm.

Embodiment 4: An Echogenic Balloon Tip with a Patterned Surface

There is a determined pattern on a surface of the metal balloon tip.

In addition, the patterned surface the balloon tip can also be covered with a heat-shrinkable polymer coating. Due to an air gap on the patterned surface, air can be trapped between the balloon tip surface and the polymer coating so as to form an air/polymer interface, the interface having a large difference in acoustic impedance, thereby improving echogenicity.

Figure 6A:
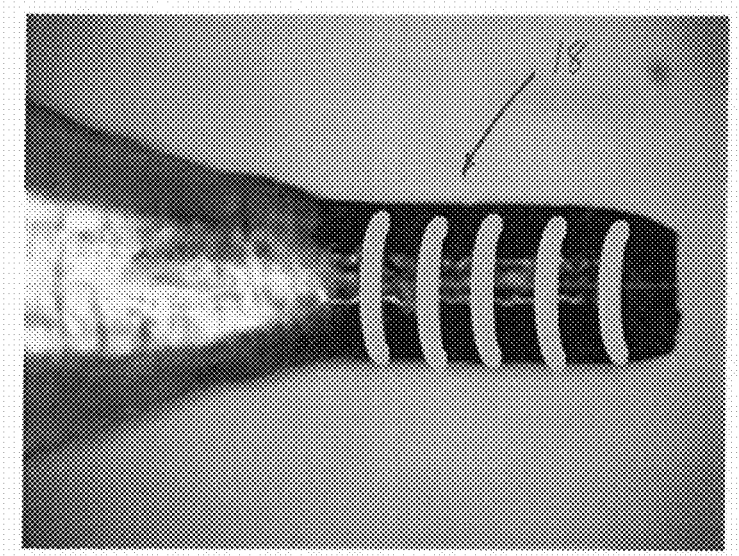
Figure 6B:
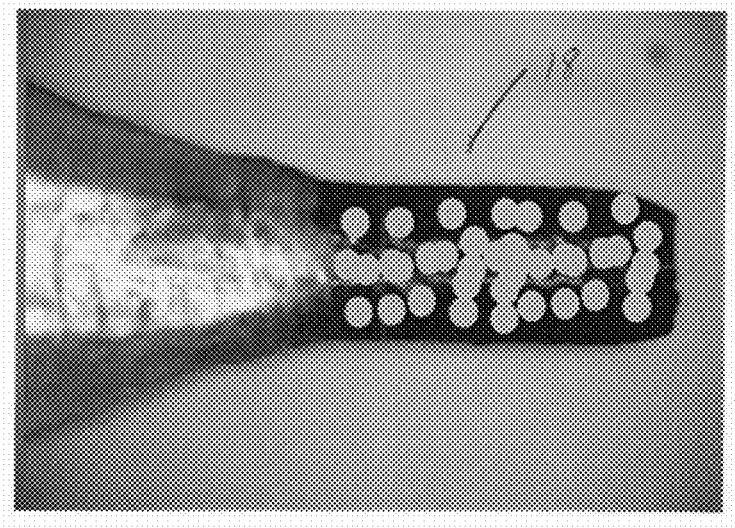
Figure 6C:
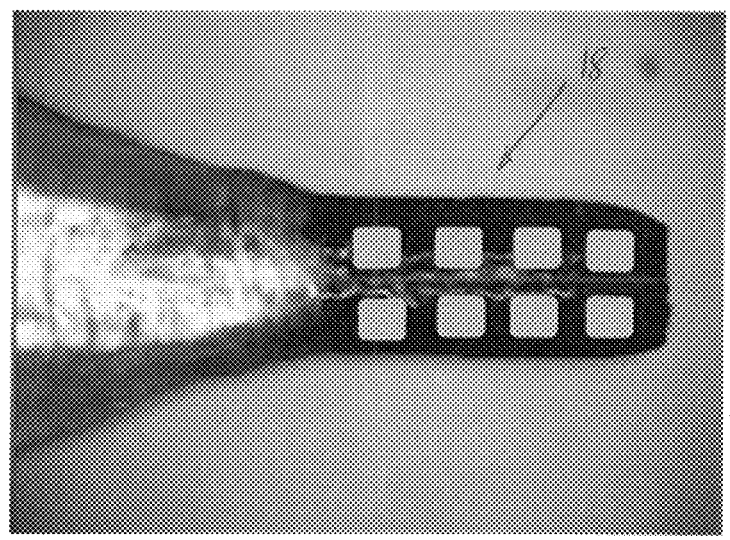

Surface patterning can be achieved by machining on the final metal balloon tip, including laser lithography, etching, stamping or ball milling after the balloon tip is molded. As shown in FIGS. 6A, 6B, 6C, the surface pattern 18 can be in any shape, such as a rectangular array, a triangular array, a hemispherical array, a diamond array, a cylindrical array, or a plurality of parallel grooves extending in the circumferential direction.

Embodiment 5: An Echogenic Balloon Tip Wound with a Metal Fiber

According to this embodiment, the tip of the echogenic balloon is wound with a metal fiber. The advantage thereof is that, on one hand, as compared to the interface between the polymer surface and the surrounding tissue, it provides an interface with a higher difference in acoustic impedance between the surface of the metal fiber and the surrounding tissue, and on the other hand, the irregular arrangement of the metal fiber layer provides an irregular surface with convexes and concaves. The fiber has a circular or rectangular shaped cross section, with a diameter of from about 0.05 mm to about 0.5 mm (for a circular cross section) or a side length of from about 0.01 mm to about 0.05 mm and from about 0.05 mm to about 0.25 mm. Metals include but are not limited to silver, platinum, gold, stainless steel, or silver-stainless steel composite material. Any metal that has good biocompatibility and can be extruded into a fiber can be used.

A Balloon Having an Echogenic Body and Cones

The present disclosure also relates to an echogenic balloon having an echogenic balloon body and balloon cones, used for percutaneous nephrolithotomy surgery.

Figure 7A:
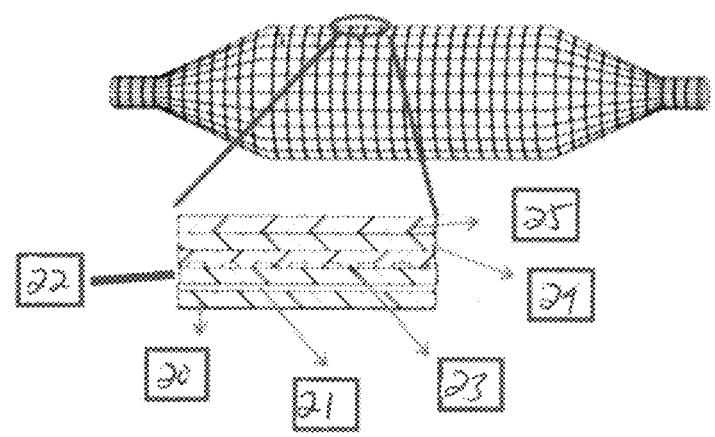
FIG. 7A shows a cross-sectional view of a prior art balloon.

As shown in FIG. 7A, as an example, the balloon may be composed of multiple layers, including a polymer base layer 20, a polymer adhesive layer 21, a polymer membrane layer 22, a polymer fiber layer 23, a polymer cladding layer 24 and an outermost polymer protective layer 25.

According to the present disclosure, an echogenic element can be added to the balloon so as to improve ultrasound echogenicity.

Figure 7B:
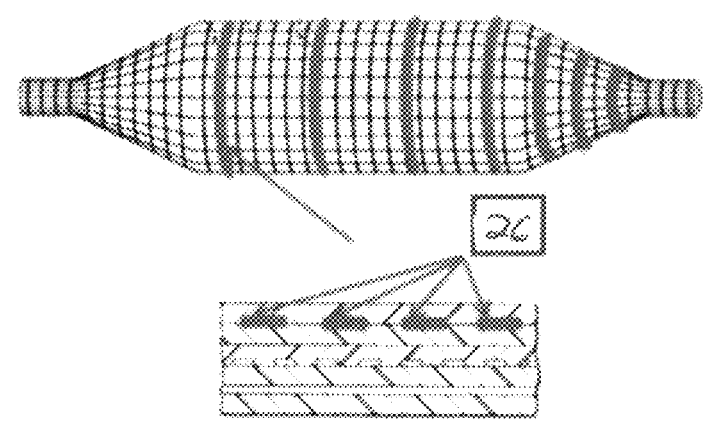
FIG. 7B shows a cross-sectional view of an echogenic balloon with metal cuffs according to the present disclosure.

Embodiment 1: An Echogenic Balloon Having an Echogenic Functional Modification as a Metal Echogenic Layer As shown in FIG. 7B, as compared to the prior art, a metal echogenic layer 26 is added as an additional layer between the polymer cladding layer 24 and the outermost polymer protective layer 25. As an alternative, it will be sufficient that a metal echogenic layer is provided under the outermost layer of the balloon. Further, in such a case, the metal echogenic layer includes a plurality of metal cuffs spaced apart in the axial direction and extending in the circumferential direction of the balloon. The metal of the cuff may include, but is not limited to, silver, gold, platinum, titanium or stainless steel, etc., so as to provide enhanced sound wave reflection. Any metal that has good biocompatibility can be used. The metal cuff on the balloon body or cones has the advantage that it can be used as a scale mark to indicate the balloon position in ultrasound diagnosis. The cuff on the area of the balloon cone can indicate whether the balloon cone is correctly placed in the renal pelvis, which is important for the surgeon to judge whether the dilation is effective. Width of the cuff on the balloon body may be from about 0.8 mm to about 3 mm, and width of the cuff on the balloon cone area may be from about 0.8 mm to about 2 mm.

Embodiment 2: An Echogenic Balloon Having an Echogenic Functional Modification as a Metal Echogenic Layer Formed by Mixing a Metal Component in the Adhesive Between Different Layers According to this embodiment, it is also possible to mix metal powder in the polymer adhesive, which can increase the density of the entire composite. According to the present disclosure, in the polymer cladding layer 24 (which also serves as an adhesive layer) for adhering the polymer fiber layer 23 to the outermost polymer protective layer 25 or in the polymer adhesive layer 21 for adhering the polymer base layer 20 to the polymer film layer 22, metal powder is mixed, especially silver, titanium, nitinol, and gold powder, the metal powder having a particle size of from about 1 μm to about 10 μm, and a content of approximately 50% to approximately 80% such that density of the entire balloon is increased, thereby enhancing the echogenicity of the balloon body or cones.

Embodiment 3: An Echogenic Balloon Having an Echogenic Functional Modification as an Echogenic Layer Having Bubbles in an Adhesive Layer According to this embodiment, it is also possible to use expansion/volatility effect of a poor solvent on a solvent-based adhesive so as to create pores in a polymer base layer of a balloon. In particular, the adhesive layer (for example, the polymer cladding layer 24 or the polymer adhesive layer 21) can be expanded by volatilization of the poor solvent. The solvent molecules penetrate into the polymer chain, but do not dissolve the polymer chain. Then, when the solvent volatilizes from the adhesive layer, the underlying polymer base layer of the balloon will shrink irregularly to form an irregular (e.g., convex and concave) surface, thereby forming echogenic gas pores. An interface between the polymer and gas pores provides a high acoustic impedance, which helps to improve echogenicity.

Further, the outermost polymer protective layer 25 may be omitted. In such a case, the polymer cladding layer 24 itself may be an adhesive. As such, it is advantageous to avoid the loss of adhesiveness caused by the formation of pores.

The following are some specific examples made according to the above embodiments:

1. Examples of an Echogenic Balloon Tip 1.1 In an example of an echogenic balloon, the tip of the balloon connected to the cone of the balloon is made of a metal material, in particular, titanium. The titanium tip of the balloon is adhered to the balloon cone. A large acoustic impedance difference between the titanium tip of the balloon and an organ tissue builds an interface on the tip with large acoustic wave backscattering, such that brightness of the titanium tip of the balloon is increased.

Another way to improve the echogenicity of the metal tip of the balloon is to form a hemispherical notch with a diameter of about 45 μm on the balloon tip by laser ablation. This also enhances the echogenicity of the balloon tip.

1.2 A metal cladding layer can be provided on the balloon tip. A stainless steel foil and a titanium foil with a thickness of about 0.05 mm are used to cover the balloon tip with the help of an adhesive so as to enhance the echogenicity.

Another way is to blast the titanium foil with a thickness of 0.05 mm and the stainless steel foil with a thickness of about 0.07 mm so as to form a rough surface with a roughness of 60-120 mesh. This rough cladding layer also enhances the echogenicity of the balloon tip.

1.3 A platinum, gold or silver cuff with a width of 1.0 mm and a thickness of 0.038 mm is adhered to the entire periphery of the balloon tip. Due to the enhanced backscattering of sound waves, brightness of the entire balloon tip is improved.

1.4 A stainless steel-silver composite fiber is used to wind around the balloon tip. A stainless steel-silver composite fiber with a diameter of about 0.076 mm is used to wind around the tip of the balloon as closely as possible. The wound composite fiber helps to greatly improve the echogenicity of the balloon tip.

1.5 A patterned balloon tip is made by machining. For example, a circle of groove is machined. As a result, an improved tip image identification is obtained, and the brightness in the grooved area is enhanced.

2. Examples of an Echogenic Balloon Body or Cone 2.1 A metal cuff is adhered to the balloon body. Particularly, a gold cuff can be adhered to the balloon body or cone to cover the entire cone. The gold cuff has a thickness of about 10 μm, and a width of about 1 mm. Echogenicity of the body or cone is improved.

2.2 A metal cuff is adhered to the balloon body. Particularly, a gold cuff can be adhered to the balloon body or cone to cover the entire cone. The gold cuff has a thickness of about 30 μm, and a width of about 1 mm. Echogenicity of the body or cone is improved.

2.3 A metal cuff is adhered to the balloon body. Particularly, a gold cuff can be adhered to the balloon body or cone to cover the entire cone. The gold cuff has a thickness of about 10 μm, and a width of about 2 mm. Echogenicity of the body or cone is improved.

2.4 Metal cuffs are adhered to the balloon body. Particularly, gold cuffs can be adhered to the balloon body or cone. The gold cuffs has a thickness of about 10 μm, and a width of about 1 mm, and an interval between adjacent gold cuffs is about 1 mm. Echogenicity of the body or cone is improved.

2.5 Metal cuffs are adhered to the balloon body. Particularly, gold cuffs can be adhered to the balloon body or cone. The gold cuffs has a thickness of about 30 μm, and a width of about 1 mm, and an interval between adjacent gold cuffs is about 1 mm. Echogenicity of the body or cone is improved.

2.6 A metal foil is adhered to the balloon body. Particularly, a stainless foil can be adhered to the balloon body or cone. The stainless cuff has a thickness of about 0.02 mm, and a width of about 1 cm. Echogenicity of the cone or body is improved.

2.7 A metal foil is adhered to the balloon body. Particularly, a titanium foil can be adhered to the balloon cone or body. The titanium foil has a thickness of about 0.05 mm, and a width of about 1 cm. Echogenicity of the cone or body is improved.

2.8 Metal powder is mixed in an adhesive between the layers. In particular, silver powder with a particle size of 6 μm is mixed into the adhesive at a content of about 50%. Echogenicity of the entire body or cone of the balloon is improved.

2.9 A layer of polyurethane adhesive is applied over a first polymer layer of the balloon (i.e. the layer that needs to be adhered to a second polymer layer). Then, a thin layer of dichloromethane or trichlormethane poor solvent is applied on top of the polyurethane adhesive to make it volatilize. Due to formation of pores in the polymer layer below the adhesive layer, echogenicity of the balloon is improved.

The above embodiments and examples improve the echogenicity of the balloon tip, balloon cone, or balloon body.

According to the present disclosure, the echogenicity of the balloon tip can also be improved by the following modifications.

A plurality of echogenic rings are mounted on the balloon tip at an axial interval. This is easy to manufacture and easy to perform ultrasonic examination.

A material for manufacturing the echogenic ring can be: a metal material with or without surface treatment; an alloy material with or without surface treatment; an polymer material with or without surface treatment and containing micro-bubbles; or any combination thereof.

Figure 8:
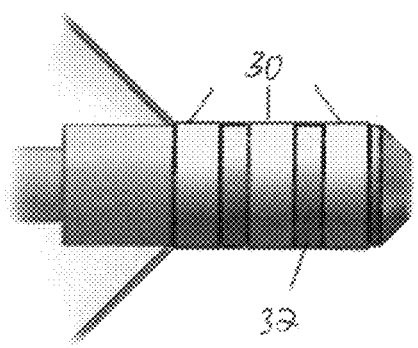
FIG. 8 shows an echogenic balloon tip mounted with a plurality of echogenic rings.

Similar to the embodiment of FIG. 5, as shown in FIG. 8, the echogenic ring 30 is mounted on the tip of the balloon outside the balloon cone, which helps to ensure a high burst pressure of the balloon and does not reduce the burst pressure of the balloon pressure.

Compared to the mounting of a single ring on the balloon tip, since multiple echogenic rings are mounted on the balloon tip at an axial interval and the surface reflection of the echogenic ring material is stronger than the surface reflection of the balloon tip material 32, more echogenic surfaces can be obtained, such that ultrasound visibility and detectability of the balloon tip can be enhanced. Further, the balloon tip material in the interval between the rings helps to trap some air during use, which also helps to enhance the ultrasound visibility of the balloon tip.

On the other hand, due to the clinical requirements, the balloon tip is usually designed to be very short. Therefore, the echogenic ring should also be small so as to engage the balloon tip without excessively increasing an outer diameter and length of the balloon tip. However, it is difficult to engage multiple rings to the balloon tip at an axial interval. This problem can be solved by an integral echogenic ring.

Figure 9A:
FIGS. 9A (side view), 9B (end view), 9C (perspective view) show an embodiment of an integral echogenic ring.
Figure 9A:
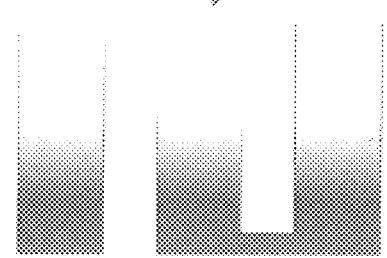
Figure 9B:
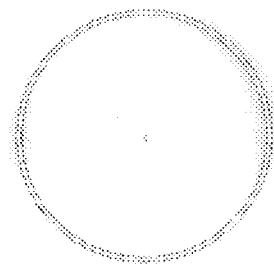
Figure 9C:
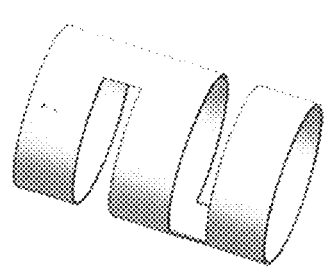
Figure 10A:
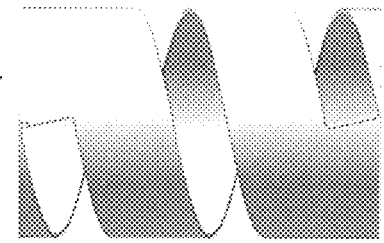
FIGS. 10A (side view), 10B (end view), 10C (perspective view) show an embodiment of an integral echogenic ring.
Figure 10B:
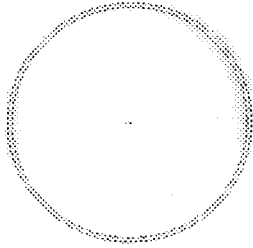
Figure 10C:
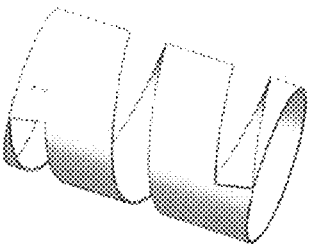
Figure 11A:
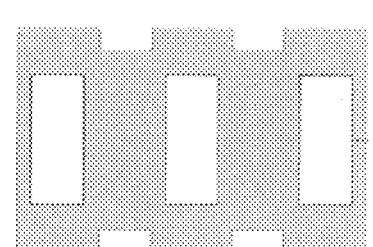
FIGS. 11A (side view), 11B (end view), 11C (perspective view) show another embodiment of an integral echogenic ring.
Figure 11B:
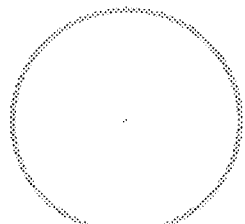
Figure 11C:
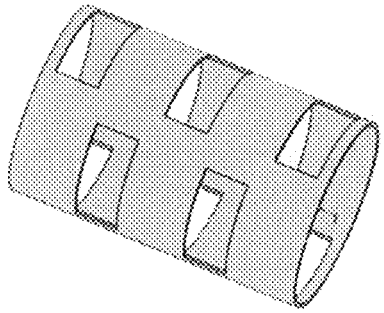

(1) As shown in FIGS. 9A (side view), 9B (end view), and 9C (perspective view), the ring body 30 is provided thereon with a plurality of circumferentially extending through grooves with opening directions opposite to each other and axially spaced from each other;

(2) As shown in FIGS. 10A (side view), 10B (end view), and 10C (perspective view), the ring body is provided thereon with a continuously spiral through groove;

(3) As shown in FIGS. 11A (side view), 11B (end view), and 11C (perspective view), the ring body is provided thereon with a plurality of axially disposed windows in which every two adjacent rows of windows are staggered from each other in the circumferential direction.

For example, the specific design requirements of the above integral echogenic ring can be as follows:

There are 2 to 5 ring bodies between the openings;

The ring body between the openings has a width of from about 0.3 mm to about 4 mm;

The opening has a width of from about 0.5 mm to about 2 mm;

The ring has a thickness of from about 0.01 mm to about 2 mm.

Scale Marks

According to another aspect of the disclosure, scale marks 40 may be printed on an outer surface of the body of the balloon 10. The scale marks 40 are visible in fluoroscopy or ultrasound, and also visible to naked eyes. The scale marks can be used to measure an insertion depth of balloon, locate an effective portion of the balloon body, and measure an affected area during surgery. The scale marks may have an internal that may be from about 1 mm to about 20 mm, for example 10 mm.

For different application purposes, a starting position of the scale marks can start at a distal shoulder 14 of the balloon 10 so as to identify a position of the effective portion of the balloon. Alternatively, they can also start at a distance D from the tip 13 of the balloon, such as about 5 mm, so as to determine the catheter insertion depth.

For easy identification, a first scale mark and another scale mark at an interval (for example, about 50 mm) are different from other scale marks, for example, one is thicker than the other.

A material for the scale mark can be: a metal material with or without surface treatment; an alloy material with or without surface treatment; a polymer material with or without surface treatment and containing micro-bubbles; or any combination thereof.

Figure 12:
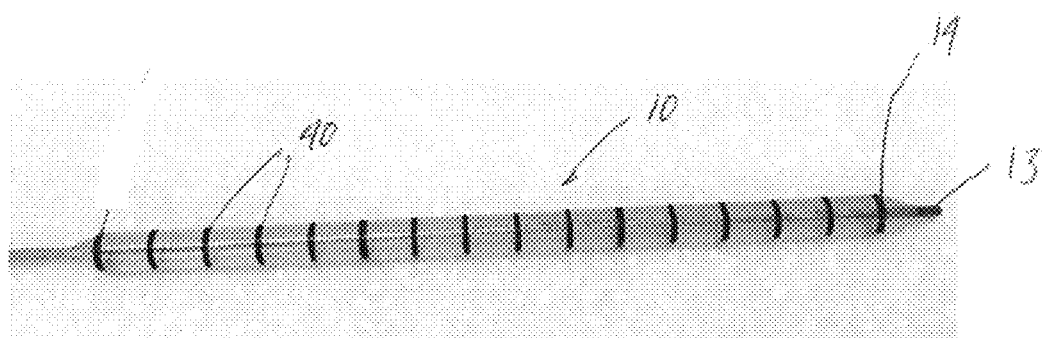
FIG. 12 shows an example of scale marks on a balloon body.

Example 1 of Scale Marks:

As shown in FIG. 12, scale marks are added on an outer surface of the balloon body, the first scale mark is located at a distal balloon shoulder and the last scale mark is located at a proximal balloon shoulder. The scale marks have an interval of 1 cm. The scale marks are visible in fluoroscopy or ultrasound, and are also visible to naked eyes.

The number of scale marks is 16 in total. The first, sixth, eleventh and sixteenth scale marks are thicker than other scale marks.

In PCNL surgery, the doctor can measure the size of calculi by comparing the size of the calculi with these scale marks in fluoroscopy or ultrasound.

In aneurysm embolization using a balloon catheter, the doctor can measure a size of a tumor neck by comparing the size of the tumor neck with these scale marks in fluoroscopy or ultrasound.

Figure 13:
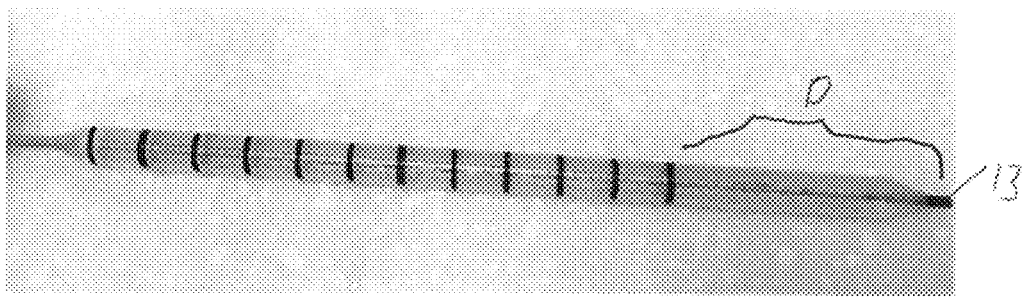
FIG. 13 shows another example of scale marks on a balloon body.

Example 2 of Scale Marks:

As shown in FIG. 13, scale marks are added on an outer surface of the balloon body, the first scale mark is about 5 mm away from a distal tip of the balloon, and the last scale mark is located adjacent a proximal end of the balloon body. The scale marks have an interval of about 1 cm. These scale marks are visible to naked eyes.

The number of scale marks is 12 in total. The first, sixth, and eleventh scale marks are thicker than other scale marks.

During PCNL surgery, the doctor needs to place the balloon in an appropriate position in the human body. The scale marks added on the outer surface of the balloon body can be used as scales to record an insertion depth of balloon. The doctor can insert the balloon and balloon catheter into the human body to a depth with naked eyes.

As used herein, the following terms have the following meanings:

"A", "an", and "the" as used herein refers to both singular and plural referents unless the context clearly dictates otherwise. By way of example, "a compartment" refers to one or more than one compartment.

"About," "substantially," or "approximately," as used herein referring to a measurable value, such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains", and are inclusive or open-ended terms that specifies the presence of what follows e.g. component and do not exclude or preclude the presence of additional, non-recited components, features, element, members, steps, known in the art or disclosed therein.

Although the invention has been described in conjunction with specific embodiments, many alternatives, modifications, and variations will be apparent to those skilled in the art. Accordingly, it embraces all such alternatives, modifications, and variations that fall within the appended claims' spirit and scope. All publications, patents and patent applications mentioned in this specification are herein incorporated in their entirety by reference into the specification, to the same extent as if each individual publication, patent or patent application was specifically and individually indicated to be incorporated herein by reference. In addition, or identification of any reference in this application shall not be construed as an admission that such reference is available as prior art to the present disclosure.

The invention claimed is:

1. A balloon for a dilatation catheter, comprising, along an axial direction of the balloon:
a balloon body,
a balloon cone at each side of the balloon body; and
a balloon tip extending from the balloon cone and fixed to the dilatation catheter,
wherein the balloon body and the balloon cone are formed of a plurality of polymer layers in a radial direction of the balloon,
wherein the balloon tip comprises metal; and
wherein the balloon tip, balloon body and balloon cones are all formed of multiple polymer layers in the radial direction of the balloon, wherein the metal of the balloon tip comprises an integral metal ring provided on the balloon tip, and a body of the ring is provided with a plurality of circumferentially extending through grooves with opening directions opposite to each other and spaced apart from each other in the axial direction.

2. The balloon according to claim 1, wherein an outer surface of the balloon body includes printed scale marks capable of reflecting ultrasonic waves.

3. The balloon according to claim 2, wherein a first scale mark and scale marks at an interval therefrom are different from other scale marks in shape.

4. The balloon according to claim 3, wherein a starting position of the scale marks starts at a distal end of the balloon or at a distance from the balloon tip.

5. A balloon for a dilatation catheter, comprising, along an axial direction of the balloon:
a balloon body,
a balloon cone at each side of the balloon body; and
a balloon tip extending from the balloon cone and fixed to the dilatation catheter,
wherein the balloon body and the balloon cone are formed of a plurality of polymer layers in a radial direction of the balloon,
wherein the balloon tip comprises metal; and
wherein the balloon tip, balloon body and balloon cones are all formed of multiple polymer layers in the radial direction of the balloon, wherein the metal of the balloon tip comprises an integral metal ring provided on the balloon tip, and a body of the ring is provided thereon with a continuously spiral through groove.

6. The balloon according to claim 5, wherein an outer surface of the balloon body includes printed scale marks capable of reflecting ultrasonic waves.

7. The balloon according to claim 6, wherein a first scale mark and scale marks at an interval therefrom are different from other scale marks in shape.

8. The balloon according to claim 7, wherein a starting position of the scale marks starts at a distal end of the balloon or at a distance from the balloon tip.

9. A balloon for a dilatation catheter, comprising, along an axial direction of the balloon:
   a balloon body,
   a balloon cone at each side of the balloon body; and
   a balloon tip extending from the balloon cone and fixed to the dilatation catheter,
   wherein the balloon body and the balloon cone are formed of a plurality of polymer layers in a radial direction of the balloon,
   wherein the balloon tip comprises metal; and
   wherein the balloon tip, balloon body and balloon cone are all formed of multiple polymer layers in the radial direction of the balloon, wherein the metal of the balloon tip comprises an integral metal ring provided on the balloon tip, and a body of the ring is provided thereon with a plurality of axially disposed windows with every two adjacent rows of windows staggered from each other in a circumferential direction.

10. The balloon according to claim 9, wherein an outer surface of the balloon body includes printed scale marks capable of reflecting ultrasonic waves.

11. The balloon according to claim 10, wherein a first scale mark and scale marks at an interval therefrom are different from other scale marks in shape.

12. The balloon according to claim 11, wherein a starting position of the scale marks starts at a distal end of the balloon or at a distance from the balloon tip.

* * * * *